United States Patent [19]

Truett

[11] Patent Number: 5,693,791
[45] Date of Patent: Dec. 2, 1997

[54] ANTIBIOTICS AND PROCESS FOR PREPARATION

[76] Inventor: William L. Truett, 42 Wolf Rd., Unit 321, Lebanon, N.H. 03766

[21] Appl. No.: 420,302

[22] Filed: Apr. 11, 1995

[51] Int. Cl.$^6$ ............... C07D 501/46; A61K 31/545
[52] U.S. Cl. ............... 540/222; 540/221; 514/202
[58] Field of Search .................. 540/222, 221; 514/202

[56] References Cited

U.S. PATENT DOCUMENTS

| | | | |
|---|---|---|---|
| 5,180,719 | 1/1993 | White et al. | 514/192 |
| 5,281,703 | 1/1994 | White et al. | 540/302 |
| 5,336,768 | 8/1994 | Albrecht et al. | 540/222 |

*Primary Examiner*—Mukund J. Shah
*Assistant Examiner*—Pavanaram K. Sripada
*Attorney, Agent, or Firm*—Herbert M. Wolfson

[57] ABSTRACT

A group of reagents, as diisocyanates, dianhydrides, diacidchlorides, diepoxides, carbodiimides and the like are utilized to link a wide variety of antibiotic moities, reacted two at a time with said reagents, the said antibiotic moieties containing groups reactive with the linking reagents as carboxylic acid, alcolhol, primary amine, and secondary amine functional groups, said functional groups being present as singularities or as multiplicities, products being readily purified using chromatographic techniques, and said products of above reactions being valuable for the treatment of microbial infections of man and animals.

4 Claims, No Drawings

ANTIBIOTICS AND PROCESS FOR PREPARATION

BACKGROUND OF THE INVENTION

This invention is concerned with the preparation of a wide variety of antibiotics of new and novel structure and antimicrobial activity. The compounds thus prepared are products from the linking of diverse antibiotic moieties via difunctional organic compounds such as diisocyanates, dianhydrides, diacidchlorides, diepoxides and carbodiimides, said antibiotics being drawn from the classes of compounds sulfonamides, penicillins and related, cephalosporins and related, quinolones, chloramphenicol, erythromycins, metronidazole, tetracyclines and aminoglycocides.

The medical literature regarding antimicrobial agents is vast and describes a number of antimicrobials including naturally occurring compounds as well as synthetic or semisynthetic compounds produced in the organic laboratory. These antimicrobial agents are classified as noted above, and there are many classes in addition to the above-noted ones.

It has been realized that the linking of two antibiotic moieties functioning in different fashions, as for example inhibiting cell-wall synthesis or protein synthesis or DNA synthesis, can be of value. Two antibiotic moieties can also be linked in which one is known to attack Gram positive bacteria and another to attack Gram negative bacteria, and this new entity is of value.

Usually the synthesis of linked antibiotics requires an extended set of organic laboratory procedures in which prior to the linkage of diverse types, such as quinolones and lactams, certain groups in the molecule must be blocked, the blocked entity then linked to a second antibiotic, which may also require blocking of some functional groups, and also the blocking groups require removal. It has been found surprisingly that a number of difunctional reagents can effect an efficient linkage of very diverse antibiotic structures. Further, the progress of the reaction can easily be followed via IR spectroscopy techniques, and the isolation of meaningful quantities achieved in facile fashion via liquid chromatography techniques.

SUMMARY OF THE INVENTION

This invention is concerned with simple methods of preparing a large number of new and novel structures possessing a wide range of antibiotic activity via linking together two antibiotic moieties.

A-L-B wherein A has the structure drawn from the following classes of antibiotics:

1. sulfonamides and related
2. penicillins and related
3. cephalosporins and related
4. quinolones
5. chloramphenicol
6. erythromycin
7. metronidazole
8. tetracyclines
9. aminoglycosides and B, drawn from the same classes.

The classes may be further characterized by the following general formulas and particular examples. L is drawn from a group of difunctional linking reagents.

1. Sulfonamides and Related

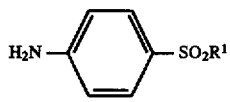

where R' is a variety of substituents.
The sulfonamides listed below are of particular interest:
A. p-aminobenzenesulfonamide
B. sulfamethoxyazole
C. acetylsulfoxazole
D. sulfamethoxypyridazine
E. sulfadiazine 2. Penicillins and Related

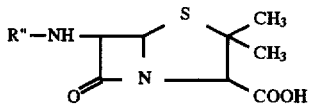

where R" is a variety of substituents. The penicillins listed below are of particular interest.
A. benzyl penicillin
B. procaine penicillin G
C. phenoxymethyl penicillin
D. ampicillin
E. amoxycillin
F. methicillin
G. oxacillin
H. cloxacillin
I. dicloxacillin
J. flucloxacillin
K. nafcillin
L. carbenicillin
M. ticaricillin
N. talampicillin
O. becampicillin
P. pivampicillin
Q. penamcarboxylic acid
R. hydroxyethyl penem
S. imipenem
T. amdinocilin 3. Cephalosporins and Related:

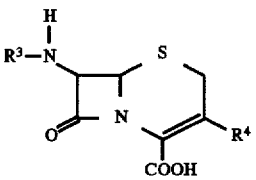

where $R^3$ and $R^4$ are a variety of substituents. The cephalosporins listed below are of particular interest.
A. cephalosporin C
B. cephalothin
C. cephaloridine
D. cephradine
E. cephazolin
F. cephalexin G. cefadroxil
H. cefaclor
I. cephamandole
J. cefuroxine
K. cefotaxime
L. ceftizoxime
M. ceftazidime
N. cefoperazone
O. cephamycin C
P. cefoxitin
Q. moxalactam 4. Quinolones

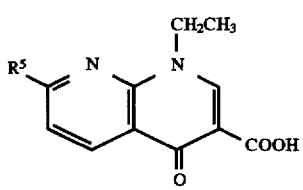

where $R^5$ is a variety of substituents and the quinoline neucleus contains fluoro atom substitution. The quinolones listed below are of particular interest.

A. nalidixic acid
B. norfloxacin
C. enoxacin
D. ciprofloxacin
E. ofloxacin

5. Chloramphenicol

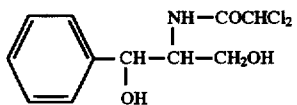

6. Erythromycin

7. Metronidazole

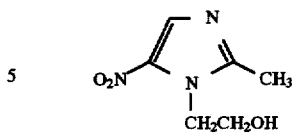

8. Tetracyclines

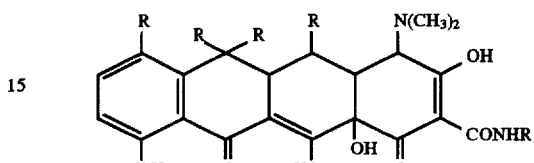

where the general formula given above is substituted to yield the particular compounds listed below.

A. tetracycline
B. oxytetracycline
C. chlortetracycline
D. rolitetracycline
E. methacycline
F. doxycycline
G. demeclocycline
H. sancycline
I. lymecycline
J. clomocycline
K. minocycline

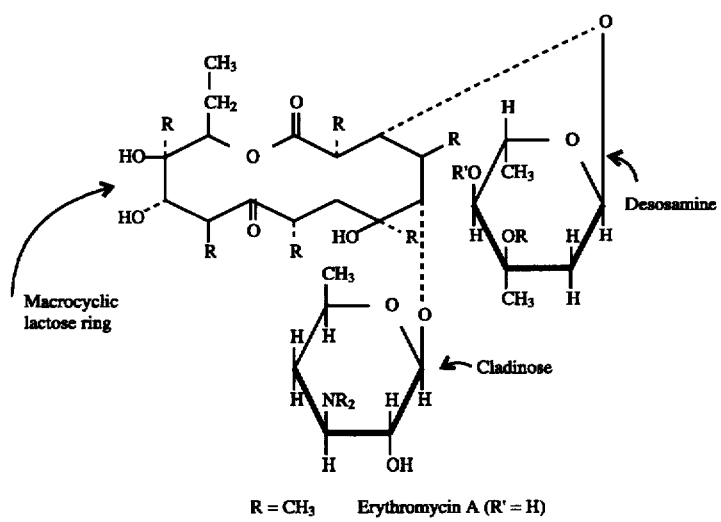

R = $CH_3$    Erythromycin A (R' = H)

9. Aminoglycosides

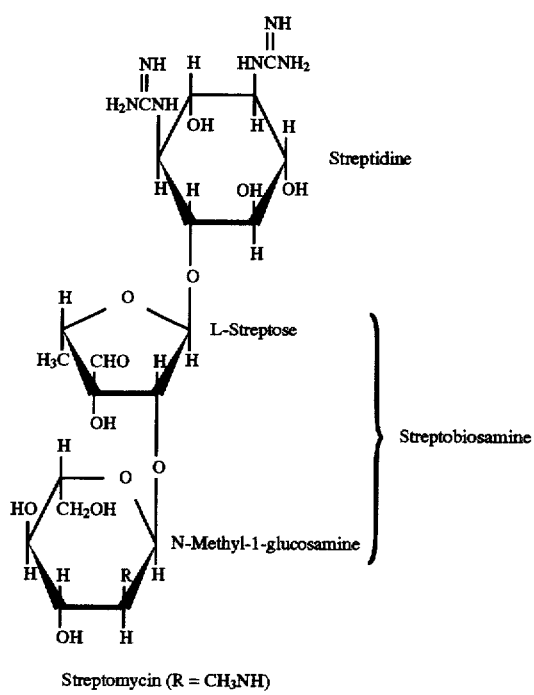

Streptomycin (R = CH₃NH)

The general formula above is variously substituted to give the particular isomers listed below.
A. streptomycin
B. tobramycin
C. kanamycin
D. amikacin
E. gentamicin Cl
F. nitilimicin
G. neomycin
H. paromomycin
I. spectinomycin The linking reagents are drawn from the type listed below.

Diisocyanates    NCO—Y—NCO

Diianhydrides

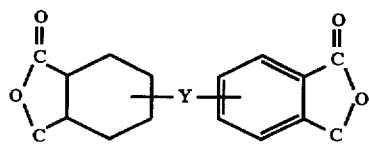

Diacidchlorides

Cl—C—Y—C—Cl

Diepoxides

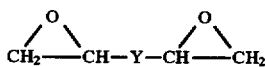
CH₂——CH—Y—CH——CH₂

Carbodiimides    Y—N=C=N—Y

In the above general formulas Y can be aliphatic, alicyclic, aromatic and heterocyclic groups.

The particular formulas for each type are listed below.
Diisocyanates:
1,6-hexamethylenediisocyanate
2,4-tolyldiisocyanate
2,6-tolyldiisocyanate
4,4'-methylene bis phenylisocyanate
4,4'-isopropylidene bis phenylisocyanate
1,4-phenyldiisothiocyanate
1,4-phenyldiisocyanate Dianhydrides
pyromellitic dianhydride
bis maleic dianhydride
3,3,4,4'-benzophenonetetracarboxylic dianhydride
1,2,6,7- hexanetetracarboxylic dianhydride
1,2,4,5- naphthalenetetracarboxylic dianhydride Diacidchlorides
terphthaloyl chloride
isophthaloyl chloride
phthaloyl chloride
adipolyl chloride
glutaryl chloride Diepoxides
1,3-butane diepoxide
1,5-cyclooctatetraene diepoxide
vinylcyclohexene diepoxide
1,4-divinylbenzene diepoxide Carbodiimides
dicyclohexylcarbodiimide
ditolylcarbodiimide Rules Based on Linking Agents Surprisingly only a few rules must be obeyed to take advantage of five different linking reagents applicable to linking two antibiotic molecules. The five linking reagents are: diisocyanates, dianhydrides, diacidchlorides, diepoxides and carbodiimides.

The types of antibiotics that can be linked are sulfonamides, trimethoprim, penicillins and related structures, cephalosporins and related structures, chloramphenicol, erythromycin, metronidazole, quinolones, tetracyclines and aminoglycosides.

The linking rules are as follows:

1. Diisocyanates can react with all acid groups, all hydroxyl groups and all primary and secondary amino groups. Thus any antibiotic moiety, A, containing a carboxylic acid, hydroxyl or amine function

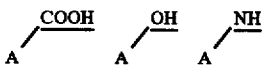

can be linked to any other antibiotic moiety B containing a carboxylic acid, hydroxyl or amine function.

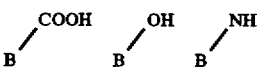

When a single antibiotic moiety contains more than a single functional group, as C,

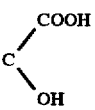

the diisocyanate can be used to link with an antibiotic moiety containing a single reactive group, as A and B above, or with an antibiotic moiety containing two functional groups as D, carboxylic acid and amine.

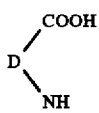

When a diisocyanate is used to link antibiotic moieties containing a plurality of groups, a mixture of products will be realized, but with chromatographic techniques the mixtures are easily separated.

Summarizing, the diisocyanate can be used to link any two antibiotics containing at least one carboxylic acid, alcohol or amino functional group, and will also effect linkage when each antibiotic moiety contains a plurality of groups.

2. Dianhydrides can be employed to link a wide variety of antibiotic moieties containing hydroxy or primary or secondary amines. The reagent will also link antibiotic molecules where each antibiotic moiety contains a plurality of hydroxy, primary and secondary amine functional groups.

3. Diacidchlorides can be employed to link a wide variety of antibiotic moieties containing hydroxyl and primary or secondary amine functional groups, and also where each moiety contains a plurality of said functions.

4. Diepoxides can be utilized to link a very wide variety of antibiotic moieties where each contains carboxylic acid, alcohol, and primary or secondary amine functional groups, or a plurality of such groups.

5. Carbodiimides can be utilized to link a wide variety of antibiotic moieties where each moiety contains at least one of the following functional groups: carboxylic acid, alcohol, and primary or secondary amine. This reagent differs from the four previously discussed since the reagent bonds the two antibiotic moieties via the removal of the elements of water from the functional groups. Moieties containing carboxylic acid groups can be linked with moieties containing carboxylic acid groups to form anhydrides. Moieties containing carboxylic acid groups can be linked to moieties containing alcohols or primary or secondary amines to form esters or amides. Moieties containing hydroxyl groups can be linked to moieties containing hydroxyl or primary or secondary amine groups to form ethers or substituted amines. Where pluralities of the carboxylic acid, hydroxyl or amine functional groups are contained in one or both antibiotic moieties, linkage will occur but the products may be complex and require chromatographic separation.

DESCRIPTION OF THE INVENTION

Section 1

The present invention describes methods for making a number of linked antibiotic molecules. The linked antibiotics are to be utilized in treating various infections in man and animals, without undue adverse side effects such as toxicity, inflammation and allergies.

There are several groups of these to-be linked compounds which can be enumerated: sulfonamides, penicillins, cephalosporins, quinolones, chloramphenicol, erythryomycin, metronidazole, tetracyclines and aminoglycosides. With each case, the antibiotics to be linked will be taken two at a time from the above groups, thus:

sulfonamide+sulfonamide
sulfonamide+penicillin
sulfonamide+cephalosporin
sulfonamide+quinolone
sulfonamide+chloramphenicol
sulfonamide+erythromycin
sulfonamide+metronidazole
sulfonamide+tetracycline
sulfonamide+aminoglycoside
penicillin+penicillin
penicillin+cephalosporin
penicillin+quinolones
penicillin+chloramphenicol
penicillin+erythromycin
penicillin+metronidazole
penicillin+tetracyclines
penicillin+aminoglycosides
cephalosporin+cephalosporin
cephalosporin+quinolone
cephalosporin+chloramphenicol
cephalosporin+erythromycin
cephalosporin+metronidazole
cephalosporin+tetracyclines
cephalosporin+aminoglycoside
quinolone+quinolone
quinolone+chloramphenicol
quinolone+erythromycin
quinolone+metronidazole
quinolone+tetracyclines
quinolone+aminoglycoside
chloramphenicol+chloramphenicol
chloramphenicol+erythromycin
chloramphenicol+metronidazole
chloramphenicol+tetacyclines
chloramphenicol+aminoglycoside
erythromycin+erythromycin
erythromycin+metronidazole
erythromycin+tetracyclines
erythromycin+aminoglycoside
metronidazole+metronidazole
metronidazole+tetracyclines
metronidazole+aminoglycoside
tetracyclines+tetracyclines
tetracyclines+aminoglycosides
aminoglycoside+aminoglycoside Within each of the above groups of antibiotics the members of each to be linked are defined as:

1. Sulfonamides:

A. p-aminobenzenesulfonamide

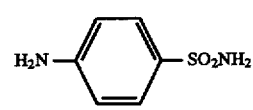

B. sulfamethoxyazole

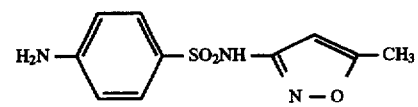

C. acetylsulfoxazole
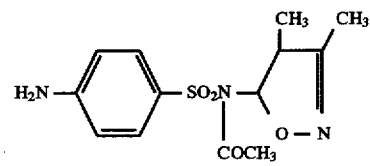
D. sulfamethoxypyridazine
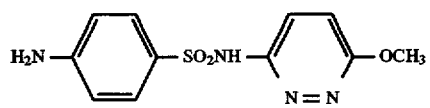
E. sulfadiazine
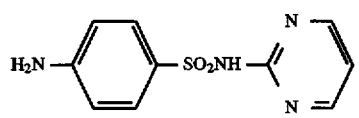
F. trimethoprim
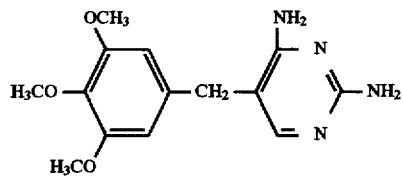
2. Penicillins:
A. benzyl penicillin
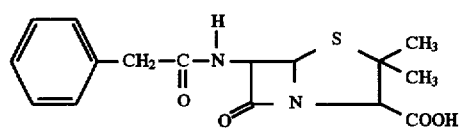
B. procaine penicillin G
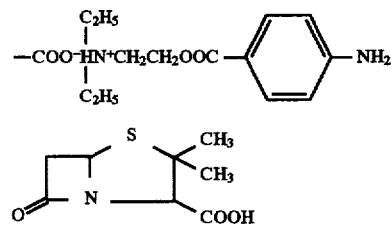
C. phenoxymethyl penicillin
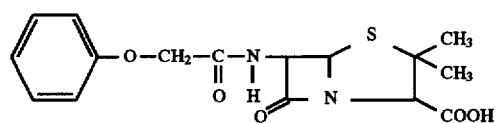
D. ampicillin
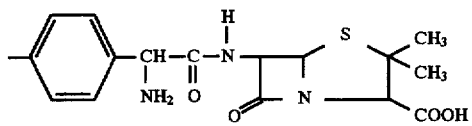
E. amoxycillin
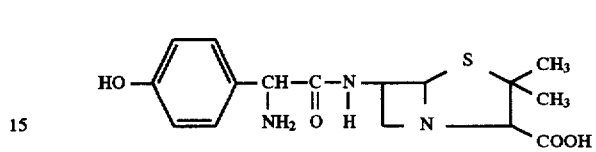
F. methicillin
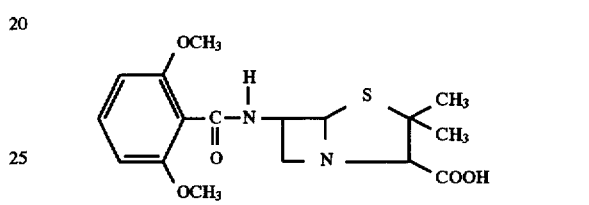
G. oxacillin
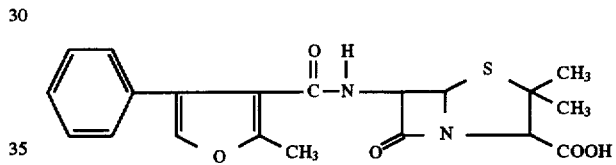
H. cloxacillin
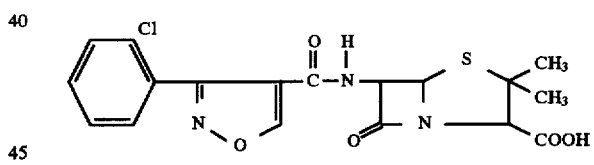
I. dicloxacillin
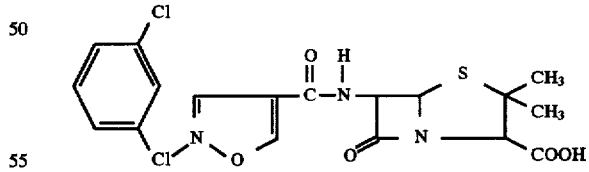
J. flucloxacillin
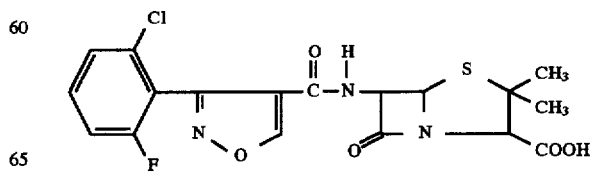

K. nafcillin
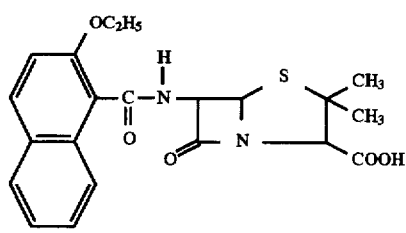
L. carbenicillin
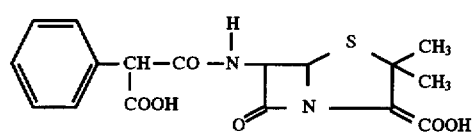
M. ticaricillin
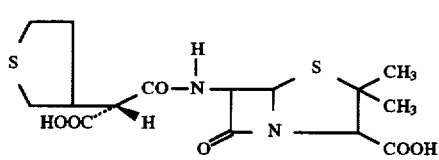
N. talampicillin
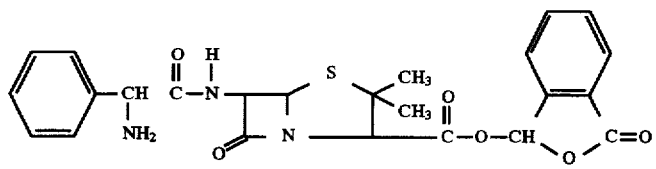
O. becampicillin
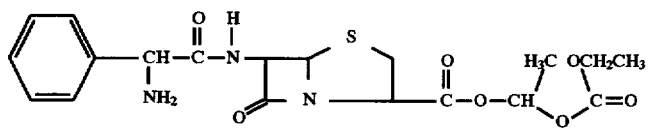
P. pivampicillin
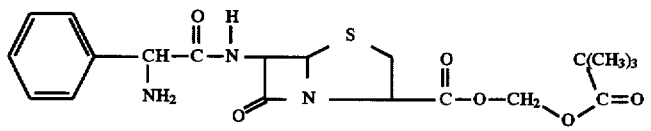
Q. penemcarboxylic acid
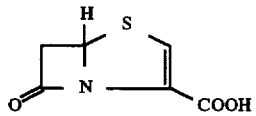
R. hydroxyethyl penem
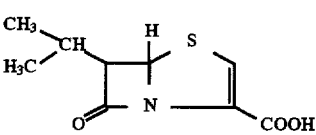
S. imipenem
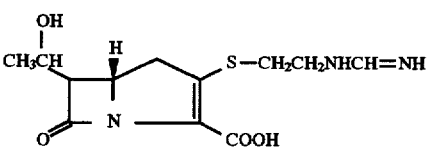
T. amdinocilin
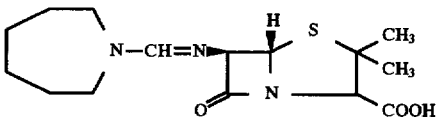

3. Cephalosporins:
A. cephalosporin C
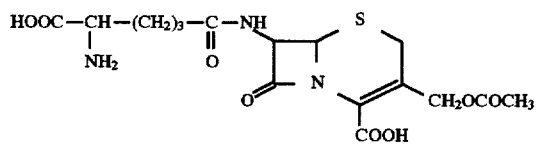
B. cephalothin
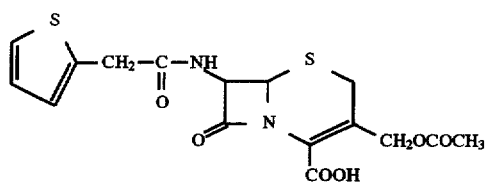
C. cephaloridine
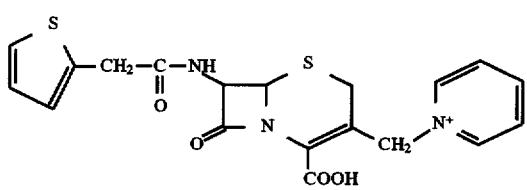
D. cephradine
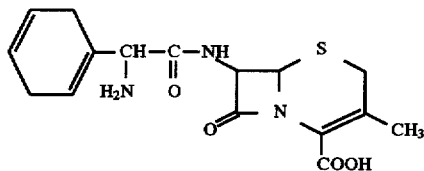
E. cephazolin
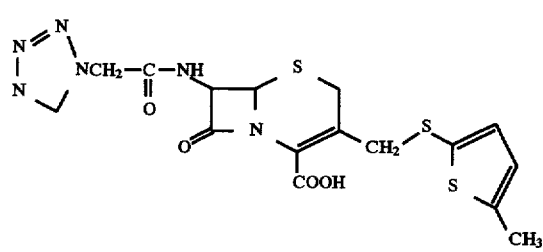
F. cephalexin
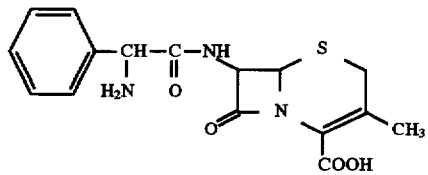
G. cefadroxil
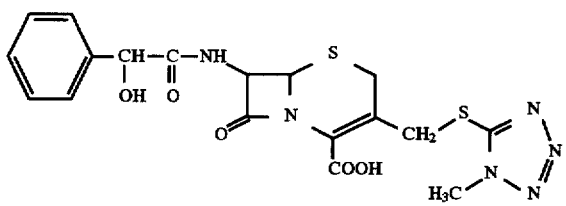
H. cefaclor
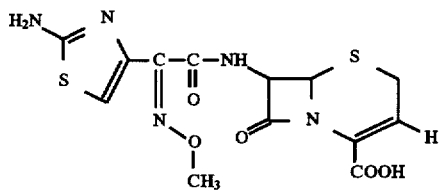 
I. cephamandole
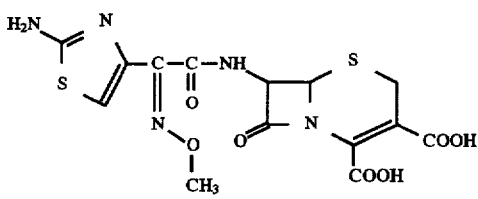
J. cefuroxine
K. cefotaxime
L. ceftizoxime M. ceftazidime
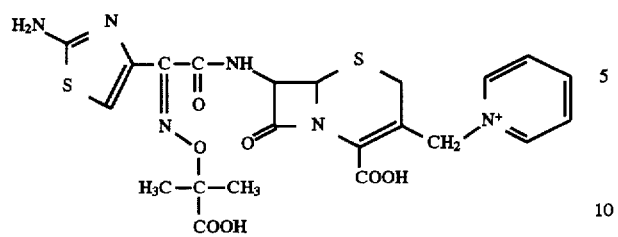
B. norfloxacin
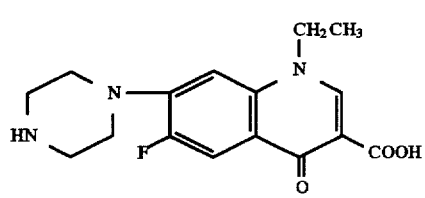
N. cefoperazone
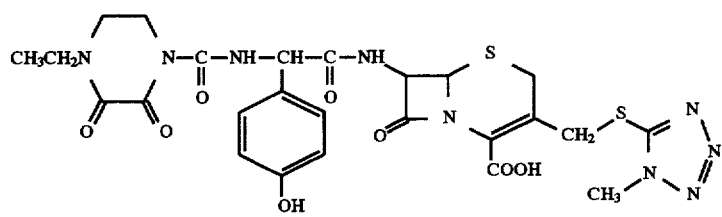
O. cephamycin C
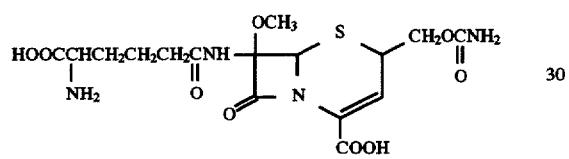
C. enoxacin
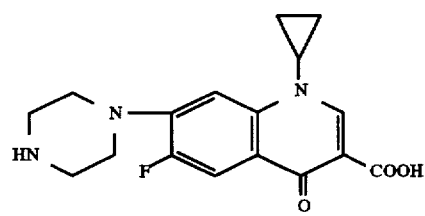
P. cefoxitin
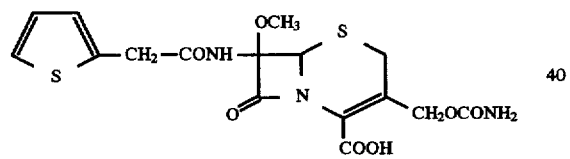
D. ciprofloxacin
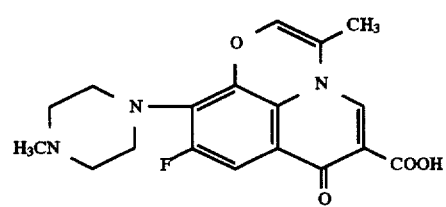
Q. moxalactam
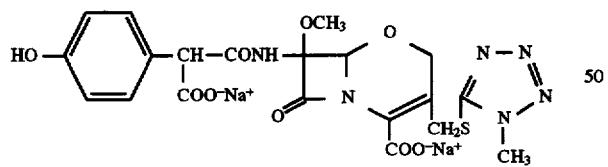
E. ofloxacin
4. Quinolones:
A. nalidixic acid
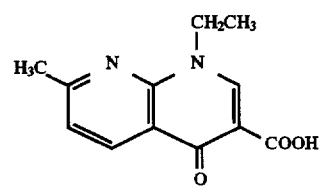
5. Chloramphenicol:
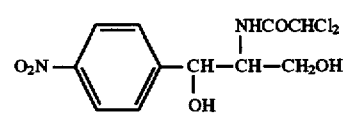

6. Erythromycin:
A. erythromycin
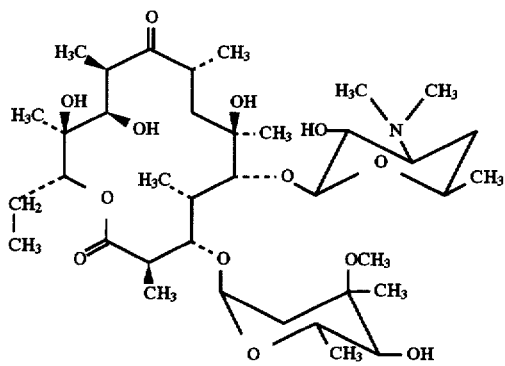
7. Metronidazole:
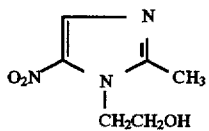
8. Tetracyclines:
A. tetracycline
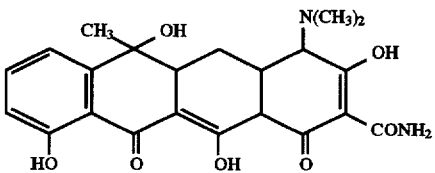
B. oxytetracycline
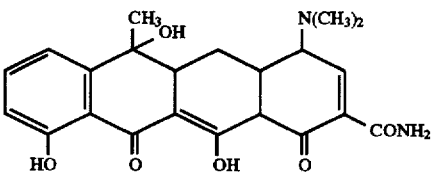
C. chlortetracycline
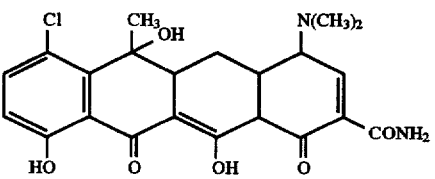
D. rolitetracycline
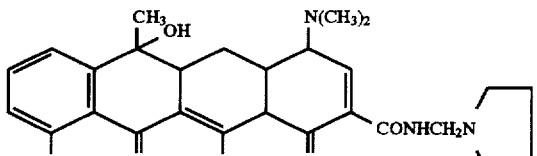
E. methacycline
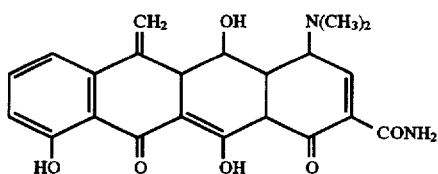
F. doxycycline
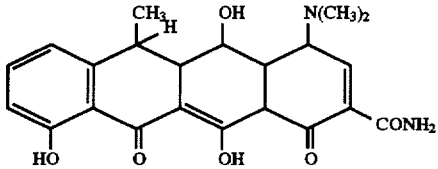
G. demeclocycline
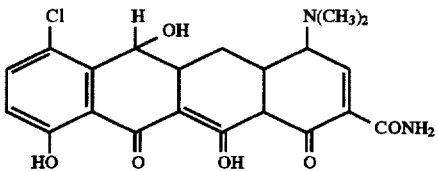
H. sancycline
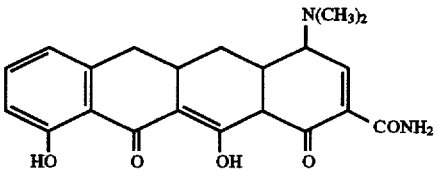
I. lymecycline
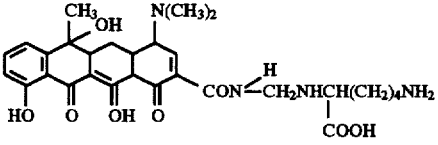

J. clomocycline
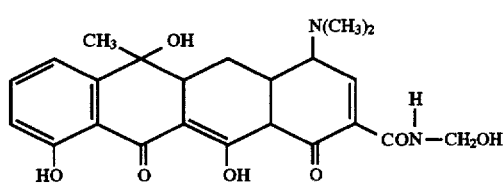
K. minocycline
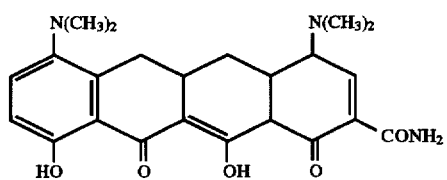
9. Aminoglycosides:
A. streptomycin
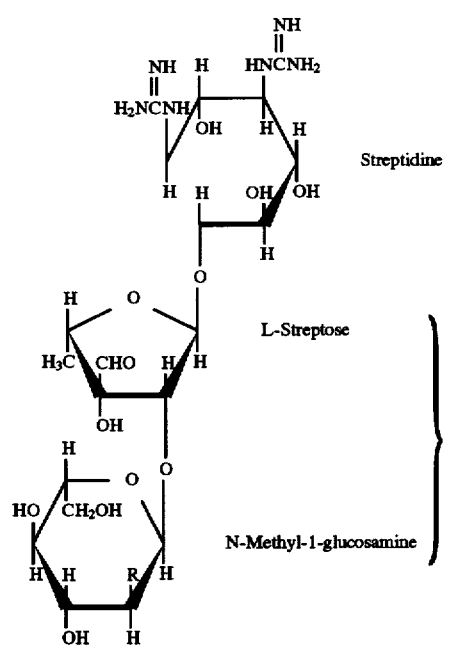
B. tobramycin
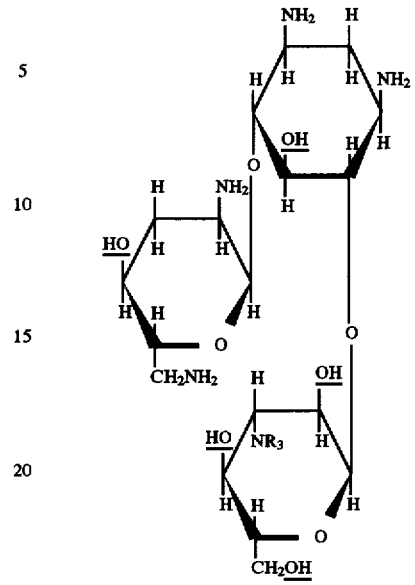
C. kanamycin
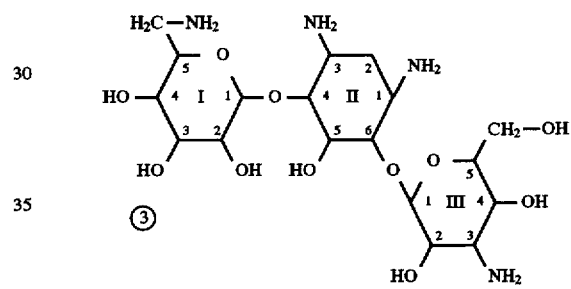
D. amikacin
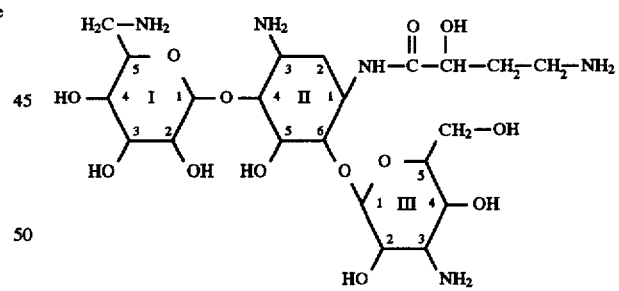

E. gentamicin Cl

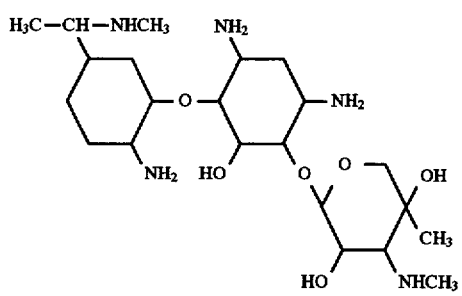

F. nitilimicin

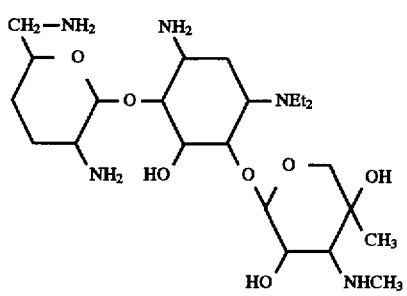

G. neomycin

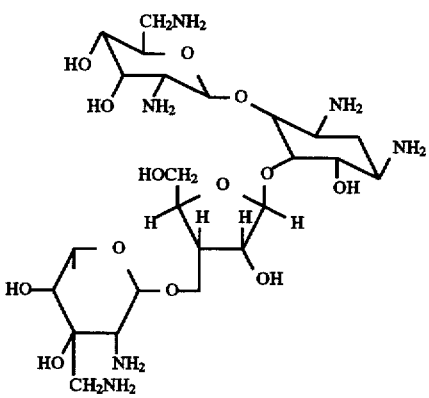

H. paromomycin

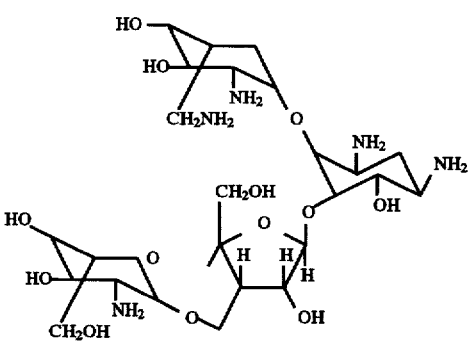

I. spectinomycin

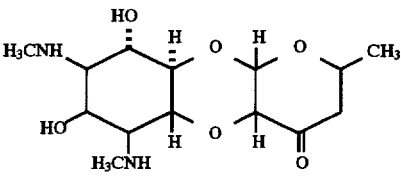

The linking agents that will be used to link the antibiotic moieties are drawn from several classes of organic molecules:
I. Diisocyanates and related structures
II. Dianhydrides
III. Diacidchlorides
IV. Diepoxides
V. Dicyclohexylcarbodiimide and related structures The class I linking agents are drawn from the group consisting of the following structures:
I. Diisocyanates and related structures:
A. hexamethylene diisocyanate $$OCN(CH_2)_6NCO$$

B. 2,4-tolyldiisocyanate

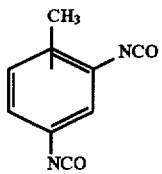

C. 2,6-tolyldiisocyanate

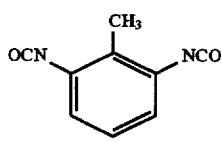

D. 4,4'-methylene-bis-phenylisocyanate

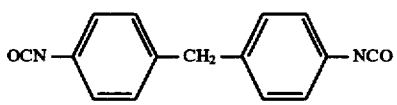

E. 4,4'-isopropylidene-bis-phenylisocyanate

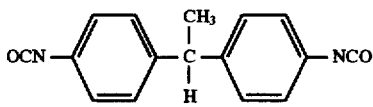

F. 1,4-phenyldiisothiocyanate

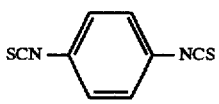

G. 1,4-phenyldissocyanate

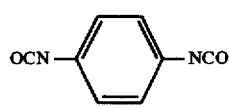

II. Dianhydrides:
A. pyromellitic dianhydride

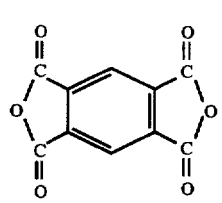

B. bismaleic dianhydride

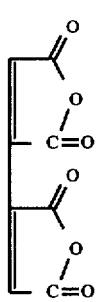

C. benzophenone, 3,3',4,4'tetracarboxylic anhydride

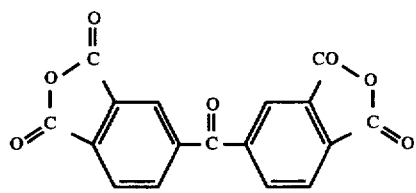

D. 1,2,6,7-hexane-tetracarboxylic anhydride

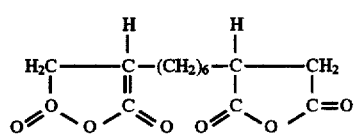

E. 1,2,5,6-naphthalene tetracarboxylic anhydride

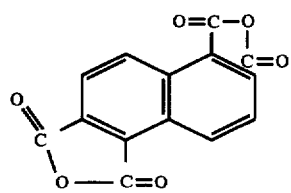

III. Diacidchlorides:
A. terphthalolyl dichloride

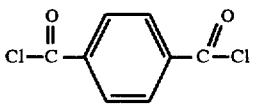

B. isophthaloyl dichloride

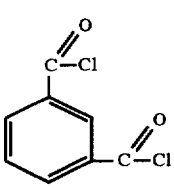

C. pthaloyl dichloride

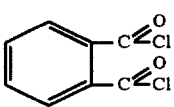

D. adipolyl chloride

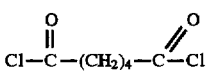

E. glutaryl chloride

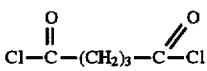

IV. Diepoxides and related structures:
A. 1,3-butadiene diepoxide

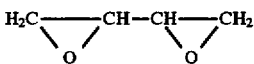

B. cyclooctatetraene diepoxide, 1.5

C. vinyl cyclohexene

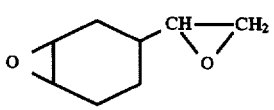

D. divinylbenzene epoxide

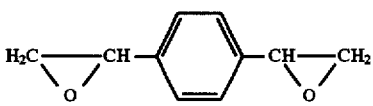

V. Carbodiimides and related structures:
A. Dicyclohexylcarbodiimide

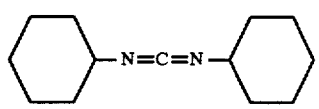

B. Ditolylcarbodiimide

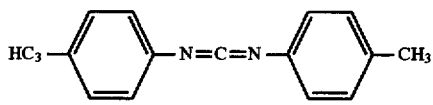

DESCRIPTION OF THE INVENTION

Section 2

Methods of Linking Antibiotic Moieties:

The structure of the two antibiotic moieties being linked will determine the nature of the particular linking agent to be employed. Thus when sulfonamides listed above are to be coupeled the basic sulfonamide structure below shows that the group which will be linking the two sulfonamide

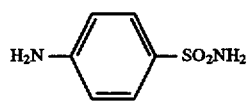

structures is the aromatic amino group. Consideration of the entire group of sulfonamides listed above will show that the only reactive group is the aromatic amino group. Of the five linking reagents listed above, four may be employed: diisocyanates, dianhydrides, diacidchlorides, and diepoxides.

The structures which result from coupling sulfonamides with sulfonamides are shown below.

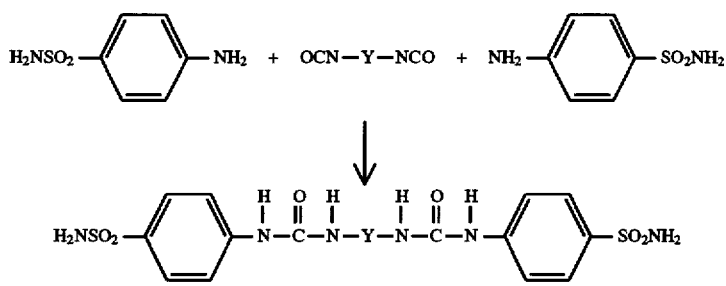

When identical sulfonamides are linked only a single product will result, but obviously when two nonidentical sulfonamides species are linked, three products will result as shown below.

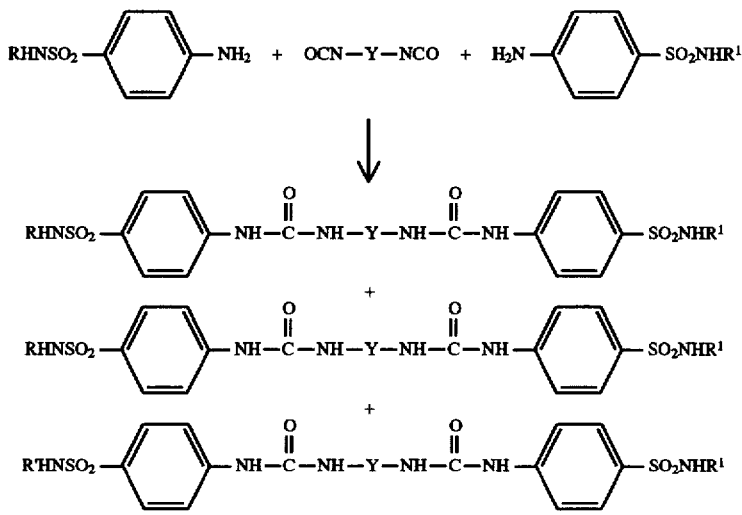

Since, in the experimental section below, equimolar quantities are used in all reactions the mixed products will predominate where the two reacting moieties have diverse structures. The modern methods of liquid chromatography render the separation of such simple mixtures, as above, to be quite simple, thus adequate material can be separated for microbial evaluation tests. Commercial quantities can be separated via preparative scale HPLC (high performance liquid chromatography).

The linking of two antibiotic moieties by utilizing dianhydrides follows a course identical to that described for diisocyanate linking agents, i.e., when a single type moiety is employed, a single product will result, but when two dissimilar moieties are employed, three products will result. As noted with diisocyanates, separation and evaluation of these products is not difficult.

single moiety resulting in a single product and two moieties resulting in three products, as shown below.

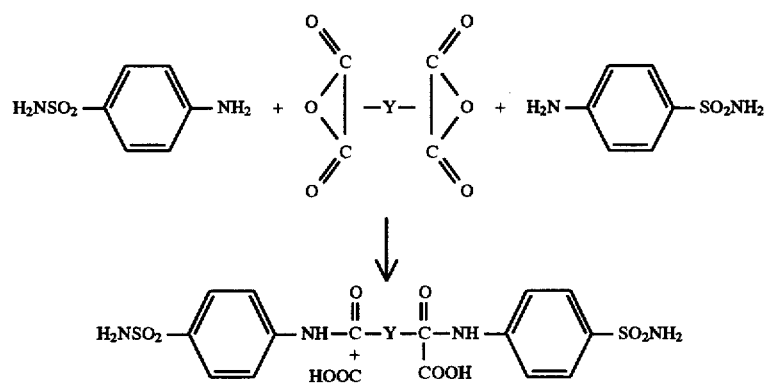

The linking of two antibiotic moieties utilizing diacid chlorides will pursue a course analagous to the reactions of diisocyanates. When a single antibiotic entity reacts with a diacid chloride a single entity results, but when two different entities react, three products are formed.

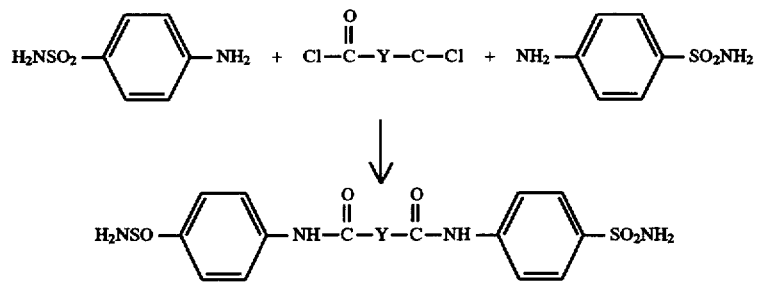

Symbolically, the three products can be seen as:

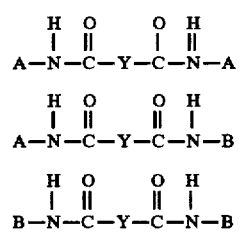

The reaction of two antibiotic moieties with a diepoxide follows a course similar to the diisocyanate reaction with a

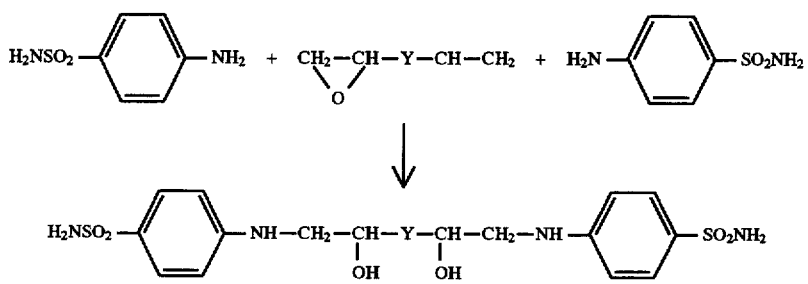

It will be noted that in the ring opening reaction the attack occurs on carbon #1 in the epoxy group predominantly.

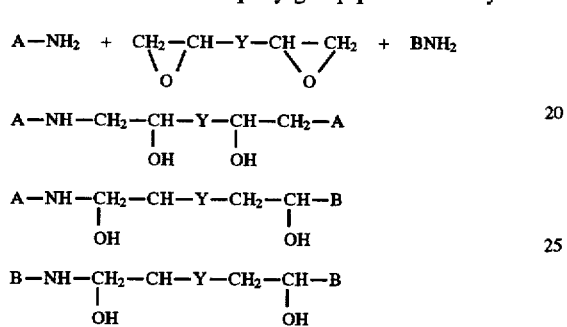

The above comments with respect to product mix apply to all antibiotic linking reactions occurring with the linking agents diisocyanates, dianhydrides, diacid chlorides, and diepoxides.

The use of the dicarbodiimides with antibiotic moieties follows a different pattern. The situation when linking antibiotic moieties via carbodiimides is the result of removing the elements of water from two moieties.

Thus the linking of two antibiotic moieties depends upon the presence of the following groups: carboxyl, amino and hydroxyl and requires a minimum total of two such groups, but with a further plurality may also be utilized. The possible combinations of the three reactive groups are five.

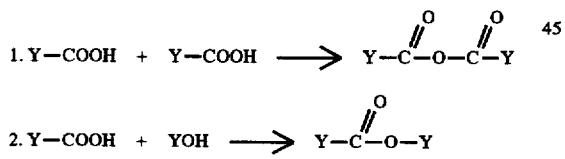

-continued

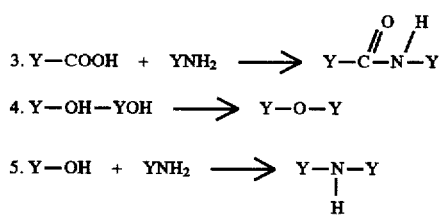

The linking of two antibiotic moieties via the groups above produces the following products:

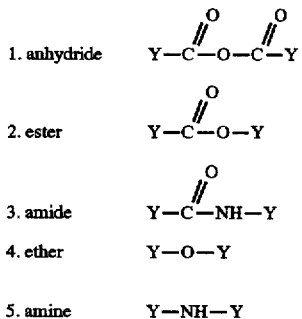

When two antibiotics are linked each containing a single reactive group, as one COOH and one $NH_2$, only a single product will result; see the example below of the reaction of dicyclohexylcarbodiimide with p-aminobenzenesulfonamide with benzylpenicillin.

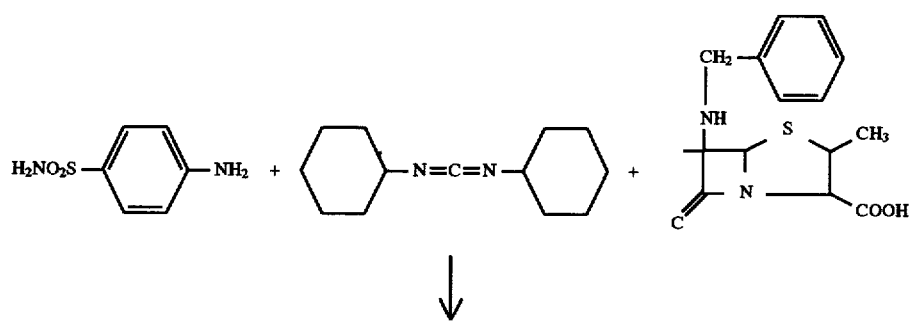

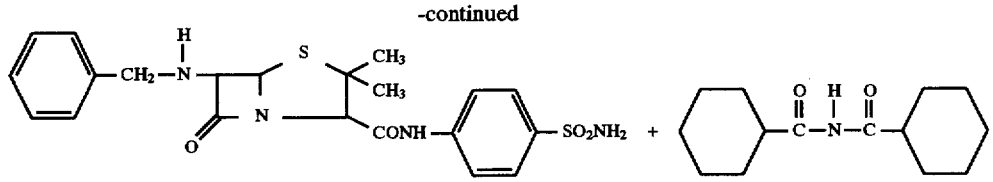

The amide product is easily separated from the by-product dicyclohexylurea by crystallization or liquid chromatography techniques.

When more than two active groups are present on a single moiety as penicillin type, carbenicillin, two products will result when linked with p-aminobenzenesulfonamide via dicyclohexylcarbodiimide, as shown below.

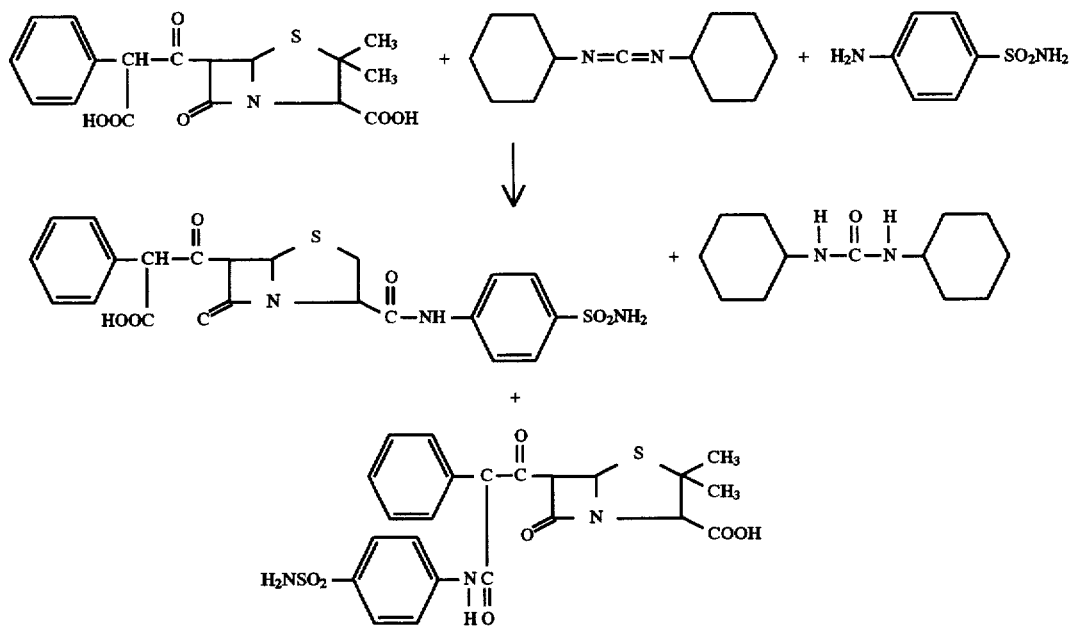

Rules are developed in the "Rules" section below to account for all products with all linking reagents linking the many antibiotic moieties.

Linking Rules

The linking rules developed below are based on the interactions of the five linking agents with a large number of eight classes of antibiotics. The classes of antibiotics and the structural formula for each entity are listed above, as well as formulas for all linking agents employed.

For purpose of developing a set of rules to link, in pairs of two, all known antibiotics, the use of the following linking reagents is designated by a Method Number in Roman numerals:

Method I—diisocyanates

Method II—dianhydrides

Method III—diacidchlorides

Method IV—diepoxides

Method V—carbodiimides

The antibiotics are from the eight classes detailed above:

1. sulfonamides and related structures, 6.
2. penicillins and related strucures, 23.
3. cephalosporins and related structure, 29.
4. quinolones (5)
5. chloramphenicol (1)
6. erythromycin (1)
7. metronidazole (1)
8. tetracyclines (11)
9. aminoglycosides (9)

Sulfonamides and trimethoprim "listings" above are as follows, with each moiety the group used in linking is noted. Also listed is the method, Roman numerals, giving the reagent used.

1. Sulfonamides and trimethoprim—link to sulfonamides and trimethoprim.

|     | Moiety                | Reactive Group  |
|-----|-----------------------|-----------------|
| SA. | sulfanilamide         | $NH_2$          |
| SB. | sulfamethoxazole      | $NH_2$          |
| SC. | acetylsulfozazole     | $NH_2$          |
| SD. | sulfamethoxypyridazine| $NH_2$          |
| SE. | sulfadiazine          | $NH_2$          |
| SF. | trimethoprim          | $NH_2$          |

SA is linked in all other moieties using Methods I, II, III, or IV. Similarly SB—SF are linked to all other moieties utilizing Methods I, II, III and IV.

2. Penicillins link to all penicillins

| | Moiety | Reactive Group |
|---|---|---|
| PA. | benzyl penicillin | COOH |
| PB. | procaine penicillin G | COOH, $NH_2$ |
| PC. | phenoxymethylpenicillin | COOH |
| PD. | ampicillin | COOH, $NH_2$ |
| PE. | amoxycillin | COOH, OH |
| PF. | methicillin | COOH |
| PG. | oxacillin | COOH |
| PH. | cloxacillin | COOH |
| PI. | dicloxacillin | COOH |
| PJ. | flucloxacillin | COOH |
| PK. | nafcillin | COOH |
| PL. | carbencillin | COOH, COOH |
| PM. | ticarcillin | COOH, COOH |
| PN. | talampicillin | $NH_2$ |
| PO. | becampicillin | $NH_2$ |
| PP. | pivampicillin | $NH_2$ |
| PQ. | penemcarboxylic acid | COOH |
| PR. | hydroxyethylpenem | COOH, OH |
| PS. | imipenem | COOH |
| PT. | cilastatin | COOH, $NH_2$ |
| PU. | amdinocillin | COOH |

Examples A–U resolve into the following types of penicillins for interaction with linking groups.

| Type | Method |
|---|---|
| COOH + COOH | I, II, IV, V |
| COOH + COOH, $NH_2$ | I, IV, V |
| COOH + COOH—OH | I, IV, V |
| COOH + COOH—COOH | I, IV, V |
| COOH + $NH_2$ | I, IV, V |
| COOH + COOH—OH | I, IV, V |
| COOH, $NH_2$ + COOH—$NH_2$ | I, II, III, IV, V |
| COOH, OH + COOH—OH | I, II, III, IV, V |
| COOH, $NH_2$ + COOH—COOH | I, IV, V |
| COOH, COOH + COOH—COOH | I, IV, V |

3. Cephalosporins link to all celphalosporins

| | Moiety | Reactive Group |
|---|---|---|
| A. | cephalosporin C | COOH, COOH, $NH_2$ |
| B. | cephalothin | COOH |
| C. | cephaloridine | COOH |
| D. | cephradine | COOH, $NH_2$ |
| E. | cephazolin | COOH |
| F. | cephalexin | COOH, $NH_2$ |
| G. | cefadroxil | COOH, $NH_2$ |
| H. | cefaclor | COOH, $NH_2$ |
| I. | cephamandole | COOH, OH |
| J. | cefuroxine | COOH |
| K. | cefotaxime | COOH, $NH_2$ |
| L. | cefizoxime | COOH, $NH_2$ |
| M. | ceftazidime | COOH, COOH, $NH_2$ |
| N. | cefoperazone | COOH, OH |
| O. | cephamycin C | COOH, COOH, $NH_2$ |
| P. | cefoxitin | COOH |
| Q. | moxalactam | COOH, COOH, OH |

Example A through Q resolve into the following types of group for cephalosporins reacting with cephalosporins.

| Type | Method |
|---|---|
| COOH + COOH | I, , IV, V |
| COOH + COOH, $NH_2$ | I, IV, V |
| COOH + COOH—OH | I, IV, V |
| COOH + COOH, COOH, $NH_2$ | I, IV, V |
| COOH + COOH, COOH, OH | I, IV, V |
| COOH—$NH_2$ + COOH—$NH_2$ | I, II, III, IV, V |
| COOH—$NH_2$ + COOH—$OH_2$ | I, II, III, IV, V |
| COOH—OH + COOH—OH | I, II, III, IV, V |
| COOH—OH + COOH, COOH, $NH_2$ | I, II, III, IV, V |
| COOH—OH + COOH, COOH, OH | I, II, III, IV, V |
| COOH, COOH, $NH_2$ + COOH, COOH, $NH_2$ | I, II, III, IV, V |
| COOH, COOH, $NH_2$ + COOH, COOH, OH | I, II, III, IV, V |

4. Quinolones linking to all quinolones

| | Moiety | Reactive Group |
|---|---|---|
| A. | nalidixic acid | COOH |
| B. | norfloxacin | COOH, NH |
| C. | enoxacin | COOH, NH |
| D. | ciprofloxacin | COOH, NH |
| E. | ofloxacin | COOH |

Examples A through E resolve into 3 types of quinolones for links to other quinolones.

| Type | Method |
|---|---|
| COOH + COOH | I, IV, V |
| COOH + COOH, NH | I, IV, V |
| COOH, NH + COOH, NH | I, II, III, IV, V |

5. Chloramphenicol linking to chloramphenicol

| | Moiety | Reactive Group |
|---|---|---|
| A. | chloramphenicol | OH, OH |

There is only one type for chloramphenicol linking to chloramphenicol

| Type | Method |
|---|---|
| OH, OH | I, II, III, IV, V |

6. Erythromycin linking to erythromycin

| | Moiety | Reactive Group |
|---|---|---|
| A. | erythromycin | 5 OH |

| Type | Method |
|---|---|
| 5 OH | I, II, III, IV, V |

7. Metronidazole linking to metronidazole

| | Moiety | Reactive Group |
|---|---|---|
| A. | metronidazole | OH |

There is a single type of linking group involved in linking metronidazole to metronidazole.

| Type  | Method        |
|-------|---------------|
| OH, OH | I, II, III, IV, V |

8. Tetracyclines linking to tetracyclines

|    | Moiety          | Reactive Group      |
|----|-----------------|---------------------|
| A. | tetracycline    | OH, OH, OH          |
| B. | oxytetracycline | OH, OH, OH, OH      |
| C. | chlortetracycline | OH, OH, OH        |
| D. | rolitetracycline | OH, OH, OH         |
| E. | methacycline    | OH, OH, OH          |
| F. | doxycycline     | OH, OH, OH          |
| G. | demeclocycline  | OH, OH, OH          |
| H. | sancycline      | OH, OH, $NH_2$, COOH |
| I. | lymecycline     | OH, OH, OH          |
| J. | clomocycline    | OH, OH, OH, OH      |
| K. | minocycline     | OH, OH              |

The linking of tetracycline to tetracycline simplifies to a single type due to the fact that OH, OH can be linked by all methods.

| Type  | Method        |
|-------|---------------|
| OH, OH | I, II, III, IV, V |

9. Aminoglycosides—link to aminoglycosides.

|    | Moiety       | Reactive Group    |
|----|--------------|-------------------|
| A. | strepomycin  | 7 OH, 2 $NH_2$    |
| B. | tobramycin   | 5 OH, 5 $NH_2$    |
| C. | kanamycin    | 7 OH, 4 $NH_2$    |
| D. | amikacin     | 8 OH, 4 $NH_2$    |
| E. | gentamicin   | 3 OH, 5 $NH_2$    |
| F. | netilmicin   | 3 OH, 5 $NH_2$    |
| G. | neomycin B.  | 7 OH, 6 $NH_2$    |
| H. | paromomycin  | 8 OH, 5 $NH_2$    |
| I. | spectinomycin | 3 OH, 2 NH       |

The linking of aminoglycoside to aminoglycoside simplifies to a single type due to the high multiplicity of OH and $NH_2$ groups.

| Type    | Method            |
|---------|-------------------|
| OH, $NH_2$ | I, II, III, IV, V |

10. Sulfonamides linking to penicillins

| Sulfonamide Type | Penicillin Type | Linking Method    |
|------------------|-----------------|-------------------|
| $NH_2$           | COOH            | I, IV, V          |
| $NH_2$           | COOH, $NH_2$    | I, II, III, IV, V |
| $NH_2$           | COOH, OH        | I, II, III, IV, V |
| $NH_2$           | COOH, COOH      | I, IV, V          |

11. Sulfonamides linking to cephalosporins

| Sulfonamide Type | Cephalosporin Type | Linking Method    |
|------------------|--------------------|-------------------|
| $NH_2$           | COOH               | I, IV, V          |
| $NH_2$           | COOH, $NH_2$       | I, II, III, IV, V |
| $NH_2$           | COOH, OH           | I, II, III, IV, V |
| $NH_2$           | COOH, COOH, OH     | I, II, III, IV, V |
| $NH_2$           | COOH, COOH, $NH_2$ | I, II, III, IV, V |

12. Sulfonamides linking to quinolones

| Sulfonamide Type | Quinolone Type | Linking Method    |
|------------------|----------------|-------------------|
| $NH_2$           | COOH           | I, IV, V          |
| $NH_2$           | COOH, NH       | I, II, III, IV, V |

13. Sulfonamides linking to chloramphenicol

| Sulfonamide Type | Chloramphenicol Type | Linking Method    |
|------------------|----------------------|-------------------|
| $NH_2$           | OH, OH               | I, II, III, IV, V |

14. Sulfonamides linking to erythromycins

| Sulfonamide Type | Erythromycon Type | Linking Method    |
|------------------|-------------------|-------------------|
| $NH_2$           | 5 OH              | I, II, III, IV, V |

15. Sulfonamide linking to metronidazole

| Sulfonamide Type | Metronidazole Type | Linking Method    |
|------------------|--------------------|-------------------|
| $NH_2$           | 5 OH               | I, II, III, IV, V |

16. Sulfonamide linking to tetracyclines

| Sulfonamide Type | Tetracycline Type | Linking Method    |
|------------------|-------------------|-------------------|
| $NH_2$           | 3 OH              | I, II, III, IV, V |
|                  | 4 OH              | I, II, III, IV, V |
|                  | 2 OH, $NH_2$, COOH | I, II, III, IV, V |

17. Sulfonamide linking to aminoglycoside

| Sulfonamide Type | Aminoglycoside Type | Linking Method    |
|------------------|---------------------|-------------------|
| $NH_2$           | n OH, n $NH_2$      | I, II, III, IV, V |

(n = 3 or greater)

18. Penicillin linking to cephalosporin

| Penicillin Type | Cephalosporin Type |
|-----------------|--------------------|
| COOH            | COOH               |
| COOH, OH        | COOH, $NH_2$       |
| COOH, $NH_2$    | COOH, OH           |
|                 | COOH, COOH, OH     |
|                 | COOH, COOH, $NH_2$ |

-continued

| Cross Types | | Linking Method |
|---|---|---|
| COOH | COOH | I, IV, V |
| COOH OH | COOH | I, IV, V |
| COOH OH | COOH, NH$_2$ | I, II, III, IV, V |
| COOH OH | COOH COOH OH | I, II, III, IV, V |
| COOH OH | COOH COOH NH$_2$ | I, II, III, IV, V |
| COOH NH$_2$ | COOH | I, IV, V |
| COOH NH$_2$ | COOH, NH$_2$ | I, II, III, IV, V |
| COOH NH$_2$ | COOH OH | I, II, III, IV, V |
| COOH NH$_2$ | COOH COOH OH | I, II, III, IV, V |
| COOH NH$_2$ | COOH COOH NH$_2$ | I, II, III, IV, V |

19. Penicillin linking to quinolones

| Penicillin Type | Quinolone Type |
|---|---|
| COOH | COOH |
| COOH NH$_2$ | COOH—NH |
| COOH OH | |
| COOH, COOH | |
| NH$_2$ | |

| Cross Types | | Linking Method |
|---|---|---|
| COOH | COOH | I, IV, V |
| COOH | COOH—NH | I, IV, V |
| COOH NH$_2$ | COOH | I, IV, V |
| COOH NH$_2$ | COOH—NH | I, II, III, IV, V |
| COOH OH | COOH | I, IV, V |
| COOH OH | COOH OH | I, II, III, IV, V |
| NH$_2$ | COOH | I, IV, V |
| NH$_2$ | COOH—NH | I, II, III, IV, V |

20. Penicillin linking to chloramphenicol

| Penicillin Type | Chloramphenicol Type | Linking Method |
|---|---|---|
| COOH | OH, OH | I, IV, V |
| COOH, NH$_2$ | OH, OH | I, II, III, IV, V |
| COOH OH | OH, OH | I, II, III, IV, V |
| COOH COOH | OH, OH | I, IV, V |
| NH$_2$ | OH, OH | I, II, III, IV, V |

21. Penicillin linking to erythromycin

| Penicillin Type | Erythromycin Type | Linking Method |
|---|---|---|
| COOH | 5 OH | I, II, III, IV, V |
| COOH, NH$_2$ | 5 OH | I, II, III, IV, V |
| COOH, OH | 5 OH | I, II, III, IV, V |
| COOH, COOH | 5 OH | I, II, III, IV, V |
| NH$_2$ | 5 OH | I, II, III, IV, V |

22. Penicillin linking to metronidazole

| Penicillin Type | Metronidazole Type | Linking Method |
|---|---|---|
| COOH | OH | I, IV, V |
| COOH, NH$_2$ | OH | I, II, III, IV, V |
| COOH, OH | OH | I, II, III, IV, V |
| COOH, COOH | OH | I, IV, V |
| NH$_2$ | OH | I, II, III, IV, V |

23. Penicillin linking to tetracyclines

| Penicillin Type | Tetracycline Type |
|---|---|
| COOH | 5 OH |
| COOH, NH$_2$ | 5 OH, 2 NH$_2$ |
| COOH, OH | 3 OH |
| NH$_2$ | 2 OH, NH$_2$, COOH |

| Cross Types | | Linking Method |
|---|---|---|
| COOH | 5 OH | I, IV, V |
| COOH | 5 OH, 2 NH$_2$ | I, IV, V |
| COOH, NH$_2$ | 5 OH | I, II, III, IV, V |
| COOH, NH$_2$ | 5 OH, 2 NH$_2$ | I, II, III, IV, V |
| COOH, OH | 5 OH | I, II, III, IV, V |
| COOH, OH | 5 OH, 2 NH$_2$ | I, II, III, IV, V |
| NH$_2$ | 5 OH | I, II, III, IV, V |
| NH$_2$ | 5 OH, 2 NH$_2$ | I, II, III, IV, V |
| NH$_2$ | 2 OH, NH, COOH | I, II, III, IV, V |

24. Penicillin linking to aminoglycosides

| Penicillin Type | Aminoglycoside Type |
|---|---|
| COOH | 3 OH, 2 NH |
| COOH, NH$_2$ | 4–8 OH, 4–6 NH$_2$ |
| COOH, OH | |
| NH$_2$ | |

Penicillin aminoglycoside cross type

| Cross Types | | Linking Method |
|---|---|---|
| COOH | 3 OH 2 NH$_2$ | I, IV, V |
| COOH NH$_2$ | 3 OH 2 NH$_2$ | I, II, III, IV, V |
| COOH OH | 3 OH 2 NH$_2$ | I, II, III, IV, V |
| NH$_2$ | 3 OH, 2 NH$_2$ | I, II, III, IV, V |
| COOH | 4–8 OH, 4–6 NH$_2$ | I, IV, V |
| COOH, NH$_2$ | 4–8 OH, 4–6 NH$_2$ | I, II, III, IV, V |
| COOH, OH | 4–8 OH, 4–6 NH$_2$ | I, II, III, IV, V |
| NH$_2$ | 4–8 OH, 4–6 NH$_2$ | I, II, III, IV, V |

25. Cephalosporin linked to quinolones

| Cephalosporin Type | Quinolone Type |
|---|---|
| COOH | |
| COOH NH$_2$ | COOH |
| COOH OH | COOH—NH |
| COOH COOH OH | |
| COOH COOH NH$_2$ | |

| Cross Types | | Linking Method |
|---|---|---|
| COOH | COOH | I, IV, V |
| COOH | COOH—NH$_2$ | I, IV, V |
| COOH—NH$_2$ | COOH | I, IV, V |
| COOH—NH$_2$ | COOH—NH | I, II, III, IV, V |
| COOH—OH | COOH | I, IV, V |
| COOH—OH | COOH—NH$_2$ | I, II, III, IV, V |
| COOH—COOH | COOH | I, IV, V |
| COOH—COOH | COOH—NH$_2$ | I, IV, V |
| COOH—COOH OH | COOH | I, IV, V |
| COOH COOH OH | COOH NH$_2$ | I, II, III, IV, V |
| COOH COOH NH$_2$ | COOH | I, IV, V |
| COOH COOH NH$_2$ | COOH NH$_2$ | I, II, III, IV, V |

26. Cephalosporin linked to chloramphenicol

| Cephalosporin Type | Chloramphenicol Type |
|---|---|
| COOH | OH OH |
| COOH, NH$_2$ | |

| -continued | | |
|---|---|---|
| COOH OH | | |
| COOH COOH OH | | |
| COOH COOH NH₂ | | |

| Cross Types | | Linking Method |
|---|---|---|
| COOH | OH OH | I, IV, V |
| COOH NH₂ | OH OH | I, II, III, IV, V |
| COOH OH | OH OH | I, II, III, IV, V |
| COOH COOH OH | OH OH | I, II, III, IV, V |
| COOH COOH NH₂ | OH OH | I, II, III, IV, V |

27. Cephalosporin linked to erythromycin

| Cephalosporin Type | Erythromycin Type |
|---|---|
| COOH | 4 OH |
| COOH NH₂ | |
| COOH OH | |
| COOH COOH OH | |
| COOH COOH NH₂ | |

| Cross Types | | Linking Method |
|---|---|---|
| COOH | 4 OH | I, IV, V |
| COOH NH₂ | 4 OH | I, II, III, IV, V |
| COOH OH | 4 OH | I, II, III, IV, V |
| COOH COOH OH | 4 OH | I, II, III, IV, V |
| COOH COOH NH₂ | 4 OH | I, II, III, IV, V |

28. Cephalosporin linked to metronidazole

| Cephalosporin Type | Metronidazole Type |
|---|---|
| COOH | OH |
| COOH NH₂ | |
| COOH OH | |
| COOH COOH OH | |
| COOH COOH NH₂ | |

| Cross Types | | Linking Method |
|---|---|---|
| COOH | OH | I, IV, V |
| COOH NH₂ | OH | I, II, III, IV, V |
| COOH OH | OH | I, II, III, IV, V |
| COOH COOH OH | OH | I, II, III, IV, V |
| COOH COOH NH₂ | OH | I, II, III, IV, V |

29. Cephalosporins linked to tetracyclines

| Cephalosporin Type | Tetracycline Type |
|---|---|
| COOH | 3 OH |
| COOH, NH₂ | 4 OH |
| COOH OH | 2 OH, NH₂ COOH |
| COOH COOH OH | |
| COOH COOH NH₂ | |

| Cross Types | | Linking Method |
|---|---|---|
| COOH | 3 OH | I, IV, V |
| COOH | 4 OH | I, IV, V |
| COOH | 2 OH NH₂ COOH | I, IV, V |
| COOH NH₂ | 3 OH | I, II, III, IV, V |
| COOH NH₂ | 4 OH | I, II, III, IV, V |
| COOH NH₂ | 2 OH NH₂ COOH | I, II, III, IV, V |
| COOH OH | 3 OH | I, II, III, IV, V |
| COOH OH | 4 OH | I, II, III, IV, V |
| COOH OH | 2 OH NH₂ COOH | I, II, III, IV, V |
| COOH COOH OH | 3 OH | I, II, III, IV, V |
| COOH COOH OH | 4 OH | I, II, III, IV, V |
| COOH COOH OH | 2 OH NH₂ COOH | I, II, III, IV, V |
| COOH COOH NH₂ | 3 OH | I, II, III, IV, V |
| COOH COOH NH₂ | 4 OH | I, II, III, IV, V |
| COOH COOH NH₂ | 2 OH NH₂ COOH | I, II, III, IV, V |

30. Cephalosporin linked to aminoglycosides

| Cephalosporin Type | Aminoglycoside Type |
|---|---|
| COOH | 3 OH, 2 NH₂ |
| COOH NH₂ | 4–8 OH, 4–6 NH₂ |
| COOH OH | |
| COOH COOH NH₂ | |
| COOH COOH OH | |

| Cross Types | | Linking Method |
|---|---|---|
| COOH | 3 OH, 2 NH₂ | I, IV, V |
| COOH | 4–8 OH, 4–6 NH₂ | I, IV, V |
| COOH NH₂ | 3 OH, 2 NH₂ | I, II, III, IV, V |
| COOH NH₂ | 4–8 OH, 4–6 NH₂ | I, II, III, IV, V |
| COOH OH | 3 OH, NH₂ | I, II, III, IV, V |
| COOH OH | 4–8 OH, 4–6 NH₂ | I, II, III, IV, V |
| COOH COOH NH₂ | 3 OH, 2 NH₂ | I, II, III, IV, V |
| COOH COOH NH₂ | 4–8 OH, 4–6 NH₂ | I, II, III, IV, V |

31. Quinolones linked to chloramphenicol

| Quinolone Type | Chloramphenicol Type |
|---|---|
| COOH | OH OH |
| COOH NH₂ | |

| Cross Types | | Linking Method |
|---|---|---|
| COOH | OH, OH | I, IV, V |
| COOH, NH₂ | OH, OH | I, II, III, IV, V |

32. Quinolone linked to erythromycin

| Quinolone Type | Erythromycin Type |
|---|---|
| COOH | 4 OH |
| COOH, NH₂ | |

| Cross Types | | Linking Method |
|---|---|---|
| COOH | 4 OH | I, IV, V |
| COOH NH₂ | 4 OH | I, II, III, IV, V |

33. Quinolone linked to metronidazole

| Quinolone Type | Metronidazole Type |
|---|---|
| COOH | OH |
| COOH NH₂ | |

| Cross Types | | Linking Method |
|---|---|---|
| COOH | OH | I, IV, V |
| COOH, NH₂ | OH | I, II, III, IV, V |

34. Quinolone linked to tetracycline

| Quinolone Type | Tetracycline Type |
|---|---|
| COOH | 3 OH |
| COOH, NH₂ | 4 OH |
| | 2 OH NH₂ COOH |

-continued

| Cross Types | | Linking Method |
|---|---|---|
| COOH | 3 OH | I, IV, V |
| COOH | 4 OH | I, IV, V |
| COOH | 2 OH NH₂ COOH | I, IV, V |
| COOH NH₂ | 3 OH | I, II, III, IV, V |
| COOH NH₂ | 4 OH | I, II, III, IV, V |

35. Quinolone linked to aminoglycosides

| Quinolone Type | Aminoglycoside Type |
|---|---|
| COOH | 3 OH, 2 NH₂ |
| COOH, NH₂ | 4–8 OH, 4–6 NH₂ |

| Cross Types | | Linking Method |
|---|---|---|
| COOH | 3 OH 2 NH₂ | |
| COOH | 4–8 OH, 4–6 NH₂ | |
| COOH—NH₂ | 3 OH, 2 NH₂ | |
| COOH NH₂ | 4–8 OH, 4–6 NH₂ | |

36. Chloramphenicol linked to erythromycin

| Chloramphenicol Type | Erythromycin Type |
|---|---|
| OH, OH | 4 OH |

| Cross Types | | Linking Method |
|---|---|---|
| OH OH | 4 OH | I, II, III, IV, V |

37. Chloramphenicol linked to metronidazole

| Chloramphenicol Type | Metronidazole Type |
|---|---|
| OH, OH | OH |

| Cross Types | | Linking Method |
|---|---|---|
| OH OH | OH | I, II, III, IV, V |

38. Chloramphenicol linked to tetracyclines

| Chloramphenicol Type | Tetracycline Type |
|---|---|
| OH, OH | 3 OH |
| | 4 OH |
| | 2 OH NH₂ COOH |

| Cross Types | | Linking Method |
|---|---|---|
| OH OH | 3 OH | I, II, III, IV, V |
| OH OH | 4 OH | I, II, III, IV, V |
| OH OH | 2 OH NH₂ COOH | I, II, III, IV, V |

39. Chloramphenicol linked to aminoglycosides

| Chloramphenicol Type | Aminoglycoside Type |
|---|---|
| OH, OH | 3 OH 2 NH₂ |
| | 4–8 OH, 4–6 NH₂ |

| Cross Types | | Linking Method |
|---|---|---|
| OH OH | 3 OH, 2 NH₂ | I, II, III, IV, V |
| OH OH | 4–8 OH, 4–6 NH₂ | I, II, III, IV, V |

40. Erythromycin linked to metronidazole

| Erythromycin Types | Metronidazole Type |
|---|---|
| 4 OH | OH |

| Cross Types | | Linking Method |
|---|---|---|
| 4 OH | OH | I, II, III, IV, V |

41. Erythromycin linked to tetracyclines

| Erythromycin Type | Tetracycline Type |
|---|---|
| 4 OH | 3 OH |
| | 4 OH |
| | 2 OH NH₂ COOH |

| Cross Types | | Linking Method |
|---|---|---|
| 4 OH | 3 OH | I, II, III, IV, V |
| 4 OH | 4 OH | I, II, III, IV, V |
| 4 OH | 2 OH NH₂ COOH | I, II, III, IV, V |

42. Erythromycin linked to aminoglycosides

| Erythromycin Type | Aminoglycoside Type |
|---|---|
| 4 OH | 3 OH, 2 NH₂ |
| | 4–8 OH, 4–6 NH₂ |

| Cross Types | | Linking Method |
|---|---|---|
| 4 OH | 3 OH, 2 NH₂ | I, II, III, IV, V |
| 4 OH | 4–6 OH, 4–6 NH₂ | I, II, III, IV, V |

43. Metronidazole linked to tetracyclines

| Metronidazole Type | Tetracycline Type |
|---|---|
| OH | 3 OH |
| | 4 OH |
| | 2 OH NH₂ COOH |

| Cross Types | | Linking Method |
|---|---|---|
| OH | 3 OH | I, II, III, IV, V |
| OH | 4 OH | I, II, III, IV, V |
| OH | 2 OH NH₂ COOH | I, II, III, IV, V |

44. Metronidazole linked to aminoglycosides

| Metronidazole Type | Aminoglycoside Type |
|---|---|
| OH | 3 OH, 2 NH₂ |
| | 4–8 OH, 4–6 NH₂ |

| Cross Types | | Linking Method |
|---|---|---|
| OH | 3 OH, 2 NH₂ | I, II, III, IV, V |
| OH | 4–8 OH, 4–6 NH₂ | I, II, III, IV, V |

45. Tetracyclines linked to aminoglycosides

| Tetracycline Type | Aminoglycoside Type |
|---|---|
| 3 OH | 3-OH, 2 NH₂ |
| 4 OH | 4–8 OH, 4–6 NH₂ |

-continued

2 OH NH$_2$ COOH

| Cross Types | | Linking Method |
|---|---|---|
| 3 OH | 3 OH, 2 NH$_2$ | I, II, III, IV, V |
| 3 OH | 3 OH, 2 NH$_2$ | I, II, III, IV, V |
| 4 OH | 4–8 OH, 4–6 NH$_2$ | I, II, III, IV, V |
| 4 OH | 4–8 OH, 4–6 NH$_2$ | I, II, III, IV, V |
| 2 OH NH$_2$ COOH | 3 OH, 2 NH$_2$ | I, II, III, IV, V |
| 2 OH NH$_2$ COOH | 4–8 OH 4–6 NH$_2$ | I, II, III, IV, V |

DESCRIPTION OF THE INVENTION

Section 3

The rules for linking the antibiotic moities are developed by considering all of the above data just concluded for linking all of the individual members of the said eight groups of antibiotics.

The linking rules are as follows:

1. Diisocyanates can react with all acid carboxyl groups, all hydroxyl groups and all primary and secondary amino groups. Thus any antibiotic moiety containing a carboxylic acid group, a hydroxyl group or an amine group, can be linked to any other antibiotic moiety also containing a carboxylic acid group, hydroxyl or amine function.

When a single antibiotic moiety contains a plurality of groups, as a carboxyl group and a hydroxyl group, or a carboxyl group and an amino group, this moiety can be linked by reaction with a diisocyanate to a second antibiotic moiety containing a plurality of groups, as a carboxyl group and a hydroxyl group, or a carboxyl group and an amino group.

When a diisocyanate is utilized to link antibiotic moieties containing a plurality of carboxyl acid, alcohol and amino groups, a mixture of products will be realized, but with chromatographic techniques the mixtures are easily separated.

Summarizing: the diisocyanate reagent can be used to link any two antibiotic moieties each containing at least one carboxylic acid, alcohol or amino functional group, and can also be used when each antibiotic contains a plurality of said groups.

2. Dianhydrides can be utilized to link a wide variety of antibiotic moitieties in which each moiety contains at least one hydroxyl or primary or secondary amine group. The dianhydride reagent can also be utilized to link antibiotic moities in which each moiety contains a multiplicity of hydroxyl or amino groups. In cases involving the linking of antibiotic moities containing a multiplicity of groups, a mix of products will be realized but can be separated easily via chromatographic techniques.

3. Diacidchlorides as a linking agent are covered by rules identical to those for dianhydrides. Diacidchlorides can be used to link a wide variety of antibiotic moieties in which each moiety contains at least one hydroxyl or amino group. The aciddichloride reagent can also be used to link antibiotic moieties where each moiety contains a multiplicity of hydroxyl or and amino groups. In cases involving a multiplicity of groups, a mixture of products will be realized which can be separated easily via chromatographic techniques.

4. Diepoxides as linking agents can be used to link antibiotic moities where each moiety contains a carboxyl, hydroxyl, or amino group, or where each moiety contains a plurality of said groups. When antibiotics possessing a plurality of such groups react with the epoxy linking agents a complex mix of products will be formed which can be separated via chromatographic techniques.

5. Carbodiimides as linking agents can be utilized to link a very large number of antibiotic types. Antibiotic moieties in which each moiety contains a single carboxyl group yield anhydrides. Antibiotic moities in which one moiety contains a carboxyl group only will react with a moiety containing a single hydroxyl group to form a single ester. Antibiotic moieties containing a plurality of carboxyl and hydroxyl groups will form a complex mixture of esters when reacted with carbodiimides. Antibiotic moieties containing a single carboxyl group will react with antibiotic moieties containing a single amino group to form a single product containing an amide group. When antibiotic moieties containing a multiplicity of carboxyl, hydroxyl and amino groups are linked via carbodiimides, a mixture of esters and amides will be formed. When antibiotic moieties containing singular hydroxyl groups or a multiplicity of hydroxyl groups are linked, the products will be singular or multicomponent ethers. The linking of antibiotic moieties containing singular or multiple hydroxyl and amino groups leads to the formation of a single substituted amine, or a multiplicity of amines. All of the mixtures generated by the above said reactions can be separated via chromatographic techniques.

DESCRIPTION OF THE INVENTION

Section 4

Experimental Procedures

General Comments—The procedures outlined and discussed below describe the experimental procedures necessary to carry out the linking procedures with the many antibiotic moieties previously described in this application.

Procedures for each linking reagent.

Coupling Reactions Using

1. Diisocyanates:

Solvents pyridine 50 ml anhydrous
  DMAC 50 ml anhydrous
  DMF 50 ml anhydrous
  N-methylpyrrolidone 50 ml anhydrous Temperature 0° to 50° C.

Time 5–10 hours

Quantities 0.01 mole each antibiotic moiety, 0.005 mole of linking reagent

Monitor via IR spectroscopy for —NCO group, 4.45μ

Work-up add water to ppt. product achieve separation of products via chromatography; TLC, column or HPLC.

Evaluation apply to streaked plate of several cultures—*E. coli*, Strep. Group A, *P. aruginosa*

Equipment 250 ml round bottom 3-neck flask equipped with glascol mantle for heating, thermometer, reflux condenser and teflon stirring bar energized by magnetic stirring.

Coupling Reactions Using

2. Dianhydrides
  Solvents Same as "1".
  Temperature Same as "1".
  Time Same as "1".
  Quantities Same as "1".

Monitor IR via 5.50 and 5.80 anhydride band
Work up See 1.
Evaluation See 1.

Coupling Reactions Utilizing

Diacid chlorides*

All same as 1, but IR monitor via 5.80 acid chloride band in IR

*Prior to the addition of water to terminate the reaction g. (0.25 ml) of sodium bicarbonate is added in small portions to neutralize all hydrochloric acid.

Coupling Reactions Utilizing

4. Diepoxides

All same as in 1, but reaction time may be extended to 24 hours to complete reaction. IR monitor via epoxide band at 9.5μ.

Coupling Reactions Utilizing

5. Carbodiimide

All same as 1, but reaction time may be as short as 1 hour. IR monitor is , via carbodiimide band at 4.50μ.
Example procedure 1. The reaction p-aminobenzene sulfonamide with sulfapyridine.

The dry pyridine solvent, 50 ml., is placed in the 250 ml round bottom flask and 1.72 g. (0.01 mole) of p-aminobenzenesulfonamide and 1.68 g. (0.01 mole) of hexyldiisocyanate is added, the temperature raised to 40° C. by means of the variac controlling the heating of the glascol mantle. The heating and stirring are continued for 4 hours, and at the end of each hour a small sample is withdrawn from the flask by means of a pippette and examined by means of IR sectroscopy. The IR spectrocopy scan is determined from 2.5 microns to 15.0 microns, and the concentration of diisocyanate is determined from the intensity of the absorption band at 4.45 microns, a band due to the —NCO group. A steady drop in the concentration of the —NCO group indicates progress of the reaction. At the end of 4 hours at 40° C. the concentration of the isocyanate group has dropped by 80 per cent. The reaction is forced to conclusion by raising the temperature to 50° C. for two hours, at the end of which time the —NCO group is not detectable by IR spectroscopy.

The reaction is terminated by the addition of 50 ml of water and the precipitated reaction product dried in a vacuum oven at 25° C. for 2 hours to yield 3.0 g., 8.8 percent. The product was evaluated for biological activity via applying a 1 percent solution in pyridine to TLC (thin layer chromatography) plates. The developing solvent used was a 10-90 mixture of acetone and methanol, and the progress was monitored by a UV light. The spots on the chromatogram were evaluated via mechanical removal and the absorbent was separated from the product fraction by dissolving in pyridine, and the pyridine solution was dried onto filter paper. Tabs of the filter paper were applied to ager culture plates streaked with standard bacterial cultures of S. aureus, E. coli and P aureginosa. Standard antibiotics, as p-aminosulfonamide and penicillins were used for comparison. All products showed modest inhibition zones in the vicinity of the filter paper tabs containing the product fractions.

Larger quantities of products are obtainable for animal testing most simply via prep scale liquid chromatography.

What is claimed is:

1. A pharmaceutical compound having the following formula

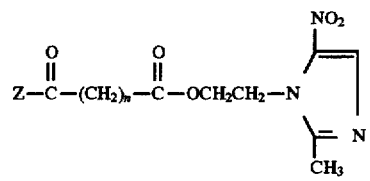

where "n" is an integer of 2–12; and where "Z" is selected from the group consisting of:

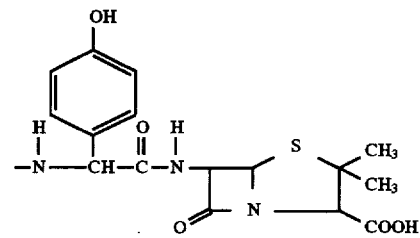

and

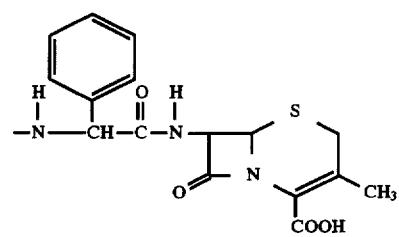

2. The compound of claim 1 wherein "n" is two.
3. The compound of claim 2 wherein "Z" is

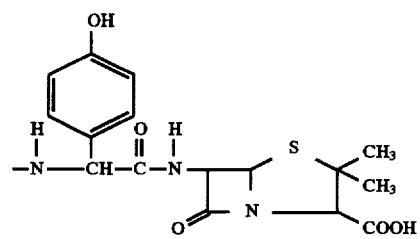

4. The compound of claim 2 where "Z" is

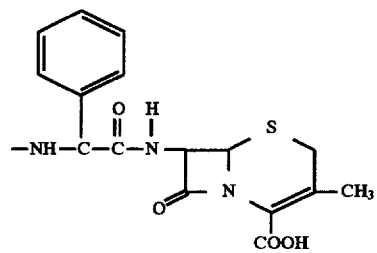

* * * * *